United States Patent [19]

Philips et al.

[11] Patent Number: 4,935,447

[45] Date of Patent: Jun. 19, 1990

[54] AGRICULTURAL GEL-FORMING COMPOSITIONS

[75] Inventors: Judson C. Philips, Gales Ferry; Hazen L. Hoyt, IV, East Lyme; Christopher A. Macri, Old Lyme, all of Conn.; Wesley L. Miller, Gainesville, Fla.; John J. O'Neill, Norwich, Conn.

[73] Assignee: Pfizer Inc., New York, N.Y.

[21] Appl. No.: 143,910

[22] Filed: Jan. 13, 1988

[51] Int. Cl.$^5$ .................... A01N 25/30; A01N 25/02; A61K 31/16

[52] U.S. Cl. .................... 514/640; 514/86; 514/119; 514/141; 514/413; 514/476; 514/365; 514/629; 514/481; 514/502; 514/493; 514/75; 514/223.8; 514/672; 71/92; 71/93; 71/118; 71/DIG. 1

[58] Field of Search ............... 71/DIG. 1, 92, 93, 118; 514/640, 86, 119, 141, 413, 465, 431, 476, 365, 629, 481, 502, 493, 75, 223.8, 672

[56] References Cited

U.S. PATENT DOCUMENTS

| | | | |
|---|---|---|---|
| 3,157,484 | 11/1964 | Swain et al. | 71/DIG. 1 |
| 4,044,708 | 1/1981 | Dellicolli et al. | 71/55 |
| 4,461,641 | 7/1984 | Abildt et al. | 71/93 |
| 4,804,399 | 8/1989 | Albrecht et al. | 71/93 |

OTHER PUBLICATIONS

Abramova, Chem. Abst., vol. 90 (1979) 108865j.
Saveler et al., Chem. Abst., vol. 83 (1975) 189360v.

Primary Examiner—Richard L. Raymond
Assistant Examiner—Mark W. Russell
Attorney, Agent, or Firm—Peter C. Richardson; Paul H. Ginsburg; Robert F. Sheyka

[57] ABSTRACT

A method is disclosed for the containment and controlled release of and the substantial reduction of the leaching from the site of application of agricultural chemicals. In the disclosed method, the agricultural chemicals are applied to the soil dispersed in an aqueous gel-forming composition. Novel compositions of the agricultural chemicals dispersed in aqueous gel-forming compositions are also disclosed.

22 Claims, 4 Drawing Sheets

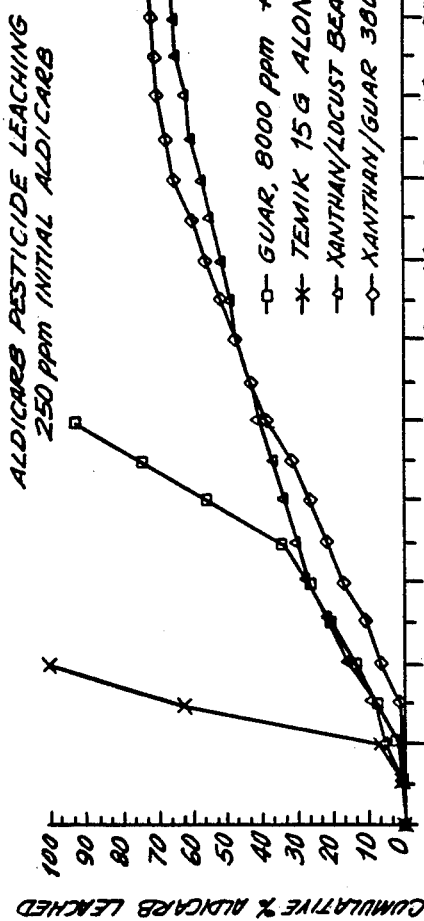
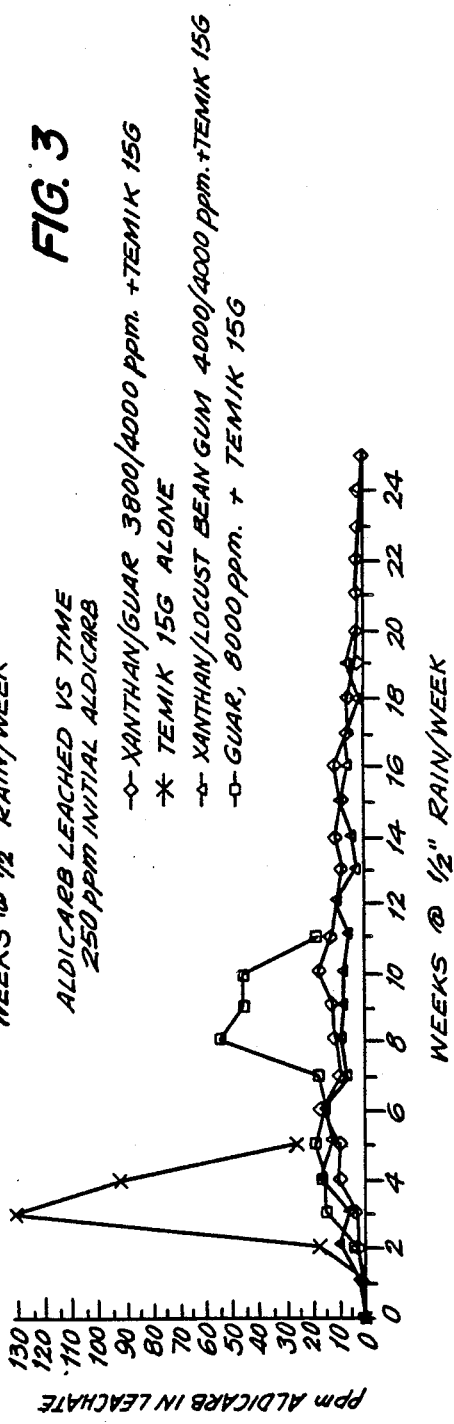
FIG. 2
FIG. 3

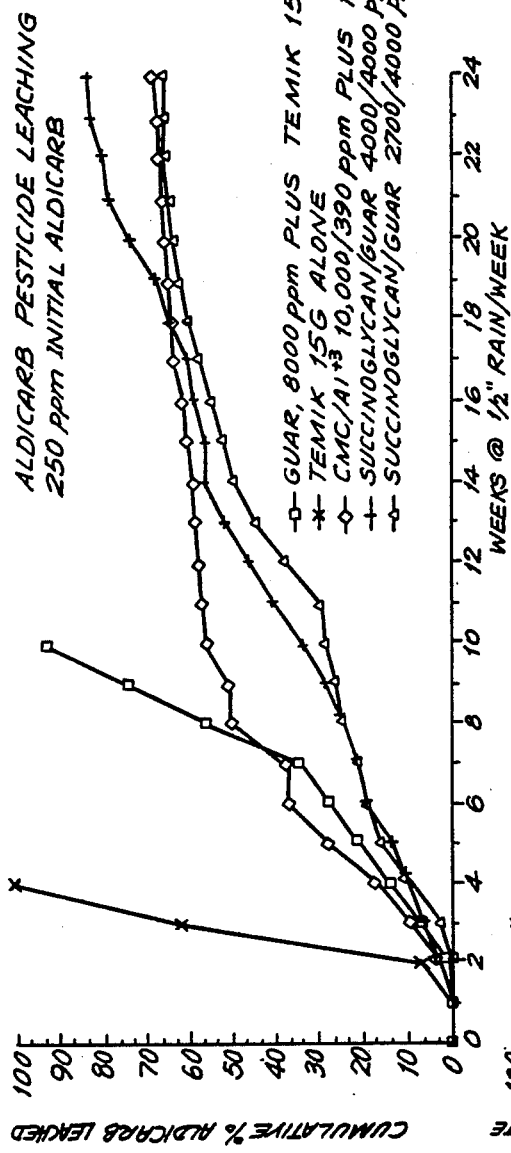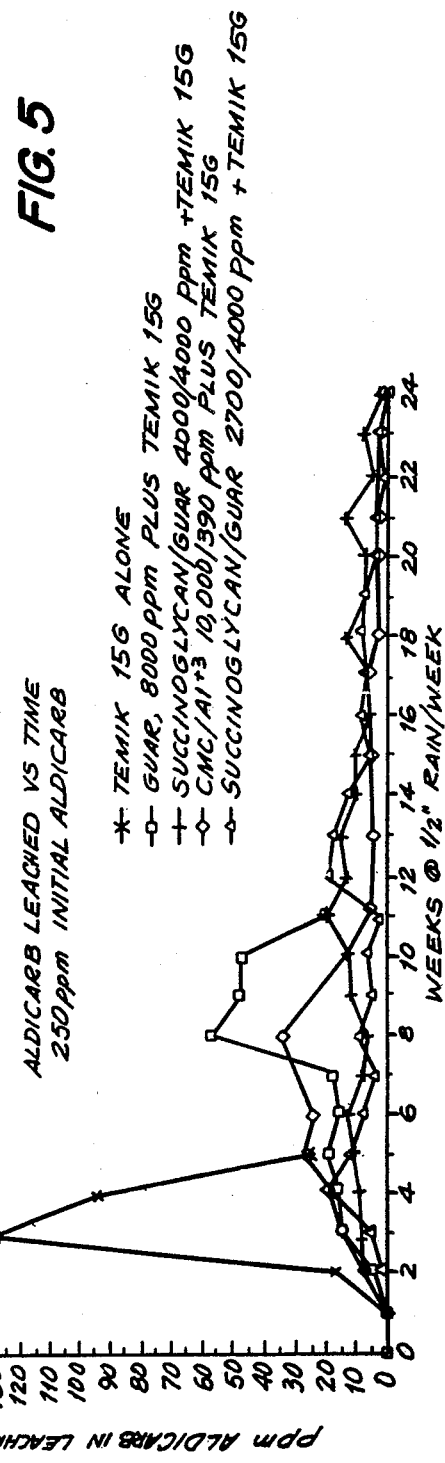

AGRICULTURAL GEL-FORMING COMPOSITIONS

The present invention relates to methods and compositions for the containment and controlled release of agriculturally active chemicals.

In recent years, the use of agriculturally active chemicals, such as pesticides, herbicides and fertilizers, has increased rapidly. While offering numerous advantages such as, for example, increased crop yield and crop size, this increased usage has also led to the development of associated problems. One of the more severe problems associated with the increased usage of agricultural chemicals has been the contamination of groundwater supplies due to leaching of the agricultural chemical from the site of application. This is a particularly serious problem in those areas where local residents are dependent upon groundwater as a source of drinking water. A number of solutions to the containment of agricultural chemicals have been suggested.

One solution is to administer the agricultural chemical in combination with a gelling agent. This process is disclosed in a number of U.S. Pat. Nos., for example, 3,836,638, 3,876,671, 4,177,056, 4,107,292, 3,562,176, 3,143,407, 3,253,984, 4,436,719 and 4,435,931. The above patents disclose either agricultural chemicals suspended in a gel or the use of gels to aid in the uniform dispersion of microencapsulated insecticides. The above patents do not disclose the use of gels formed by cross-linking a water-soluble polymer with a polyvalent metal cation nor do they disclose other cross-linked gels.

U.S. Pat. No. 4,401,456 teaches the use of alginate gel beads containing bioactive materials dispersed therein. The teachings of the patent are directed solely to the use of alginate cross-linked with a metal cation as the gelled composition containing the bioactive material and there is no suggestion that other cross-linked gels can be used.

U.S. Pat. No. 4,440,746 discloses a granular pesticide composition prepared by reacting a polyvinyl alcohol, a pesticide and a borate in water until a gel is formed, drying the gel and then grinding the product to the desired particle size. The teachings of this patent are directed to the formation of the granular pesticide and require that the pesticide be soluble in polyvinyl alcohol.

U.S. Pat. No. 3,659,026 discloses an agricultural chemical incorporated into a xanthan/locust bean gum gel-forming composition. In this patent, the agricultural chemical/xanthan/locust bean gum composition is applied by spraying onto the leaves of the plants.

Thus, there remains a need for both an effective process and an effective composition for the containment of agricultural chemicals.

SUMMARY OF THE INVENTION

In one embodiment, the present invention is directed to a process for the controlled release and substantial reduction of leaching from the site of application of agricultural chemicals selected from the group consisting of pesticides, fumigants and herbicides, and decomposition products thereof, comprising administering said chemical dispersed in an aqueous gel-forming composition formed by combining (a) an effective amount of a water soluble polymer selected from the group consisting of polymers produced by bacteria of the genus Xanthomonas, polymers produced by bacteria of the genera Agrobacterium and Pseudomonas, hydroxyethylcarboxymethylcellulose, carboxymethylcellulose, guar gums, polyacrylamides, and derivatives thereof, with (b) an effective amount of at least one polyvalent metal cation capable of cross-linking said polymer, said cross-linking agent selected from the group consisting of aluminum (III), tin (IV), chromium (III), antimony (V), iron (III), titanium (IV) and zirconium (IV) and (c) aqueous media.

A preferred gel-forming composition is formed by cross-linking carboxymethylcellulose with aluminum (III). Another preferred gel-forming composition is formed by cross-linking Xanthan gum with aluminum (III). Yet another preferred gel is formed by cross-linking a succinoglycan with aluminum (III).

Particularly preferred agricultural chemicals are organic pesticides and organic fumigants with a preferred organic pesticide being 2-methyl-2-(methylthio)propanal 0-[-methylamino)carbonyl]oxime and a preferred organic fumigant being N-methyldithiocarbamate. Organic herbicides can also be used in the process of the present invention.

In another embodiment, the present invention is directed to a process for the controlled release and prevention of leaching from the site of application of agricultural chemicals selected from the group consisting of pesticides, herbicides and fumigants, and decomposition products thereof, comprising administering said chemical into the soil surrounding the plants dispersed in an aqueous gel-forming composition formed by combining an effective amount of a polymer produced by bacteria of the genus Xanthomonas with a galactomannan. Preferred galactomannans are locust bean gum and guar gum, or derivatives thereof. Preferred agricultural chemicals are pesticides, herbicides and fumigants.

In another embodiment, the present invention is directed to a process for the controlled release and prevention of leaching from the site of application of agricultural chemicals selected from the group consisting of pesticides, herbicides and fumigants, and decomposition products thereof, comprising administering said chemical dispersed in an aqueous gel-forming composition formed by combining an aqueous polymerizable silicate with an acid-generating polymerization catalyst. In another preferred embodiment, a polymerization catalyst buffering compound is added to the aqueous polymerizable silicate/acid generating polymerization catalyst gel-forming composition.

In still another embodiment, the present invention is directed to a process for the substantial reduction of leaching away from the site of application and controlled release of agricultural chemicals selected from the group consisting of pesticides, herbicides and fumigants, and decomposition products thereof, comprising administering said chemical dispersed in an aqueous gel-forming composition formed by combining a compound selected from the group consisting of phenol, catechol, resorcinol, hydroquinone, sulfomethylated melamines, and aminoalkylated polyacrylamides, with an aldehyde or dialdehyde cross-linking agent of from 1 to 6 carbon atoms, the concentrations of said compound and said cross-linking agent being controlled so as to yield an aqueous gel-forming composition. Preferred gel-forming compositions are prepared by combining resorcinol and formaldehyde so as to provide a composition wherein the total concentration of each is from about 0.25 to about 5.0 weight percent. Another preferred gel-forming composition is formed by combining a sulfurous acid salt, melamine and an aldehyde in specified proportions so as to yield a gel-forming composition. Another preferred gel-forming composition is formed by cross linking an aminomethylated polyacrylamide with glyoxal.

In another embodiment, the present invention is directed to a gel-forming composition formed by combining a polymer produced by bacteria of the genera Agrobacterium or Pseudomonas with a galactomannan. Preferred galactomannans are locust bean gum and guar gum. Also preferred are agricultural chemicals incorporated into these aqueous gel-forming compositions.

In yet another embodiment, the present invention comprises novel agricultural chemical containing compositions, said composition when applied exhibiting controlled release and substantially reduced leaching from the site of application of said agricultural chemical, said composition comprising an effective amount of an agricultural chemical selected from the group consisting of pesticides, herbicides and fumigants dispersed in an aqueous gel-forming composition formed by combining (a) an effective amount of a polymer selected from the group consisting of polymers produced by bacteria of the genus Xanthomonas, polymers produced by bacteria of the genus Agrobacterium and Pseudomonas, hydroxyethylcarboxymethylcellulose, carboxymethylcellulose, guar gums, polyacrylamides, and derivatives thereof, with (b) an effective amount of at least one polyvalent metal cation capable of cross-linking said polymer, said metal cation selected from the group consisting of aluminum (III), tin (IV), chromium (III), antimony (V), iron (III), titanium (IV), and zirconium (IV), and (c) aqueous media.

The agricultural chemical can be a pesticide, fumigant or herbicide with a preferred pesticide being 2-methyl-2-(methylthio)propanal 0-[(methylamino)carbonyloxime and a preferred fumigant being N-methyldithiocarbamate. In the composition of the present invention, the agricultural chemical is generally present in an amount ranging from about 0.002 to about 0.1 percent by weight and said aqueous gel-forming composition is present in an amount ranging from about 0.05 to about 1.0 percent, by weight of the total composition.

In another embodiment, the present invention is directed to an agricultural chemical containing composition, said composition when applied exhibiting controlled release and substantially reduced leaching from the site of application of said agricultural chemical, said composition comprising an effective amount of an agricultural chemical dispersed in an aqueous gel-forming composition, said gel-forming composition formed by combining an aqueous polymerizable silicate with an acid generating polymerization catalyst. If desired, additional polymerization catalyst buffering compounds may be added.

In another embodiment, the present application is directed to an aqueous gel-forming composition formed by combining a polymer produced by bacteria of the genera Agrobacterium or Pseudomonas with a galactomannan. A preferred galactomannan is locust bean gum.

In another embodiment, the present invention comprises an agricultural chemical containing composition, said composition when applied exhibiting controlled release and substantially reduced leaching from the site of application of said agricultural chemical, said composition comprising an effective amount of an agricultural chemical dispersed in an aqueous gel-forming composition, said gel-forming composition formed by combining a polymer produced by bacteria of the genera Pseudomonas or Agrobacterium with a galactomannan. Preferred galactomannans are locust bean gum and guar gum.

In another embodiment, the present invention is directed to an agricultural chemical containing composition, said composition when applied exhibiting controlled release and substantially reduced leaching from the site of application of said agricultural chemical, said composition comprising an effective amount of an agricultural chemical dispersed in an aqueous gel-forming composition, said gel-forming composition formed by combining in aqueous media a compound selected from the group consisting of phenol, resorcinol, catechol, hydroquinone, sulfomethylated melamines, and aminoalkylated polyacrylamides with an aldehyde or dialdehyde cross-linking agent of from 1 to 6 carbon atoms, the concentration of said compound and said cross-linking agent being controlled so as to yield an aqueous gel-forming composition. Preferred gel-forming compositions are prepared by combining resorcinol and formaldehyde so as to provide a composition wherein the total concentration of each is from about 0.25 to about 5.0 weight percent. Another gel-forming composition is formed by combining a sulfurous acid salt, melamine and an aldehyde in specified proportions so as to yield a gel-forming composition. Another gel forming composition is formed by combining an aminomethylated polyacrylamide with an aldehyde.

BRIEF DESCRIPTION OF THE DRAWINGS

FIGS. 1–5 are graphical representations of the percentage of aldicarb leachage into soil with and without being incorporated into the gel-forming composition of the present invention.

DETAILED DESCRIPTION OF THE INVENTION

Figure 1:
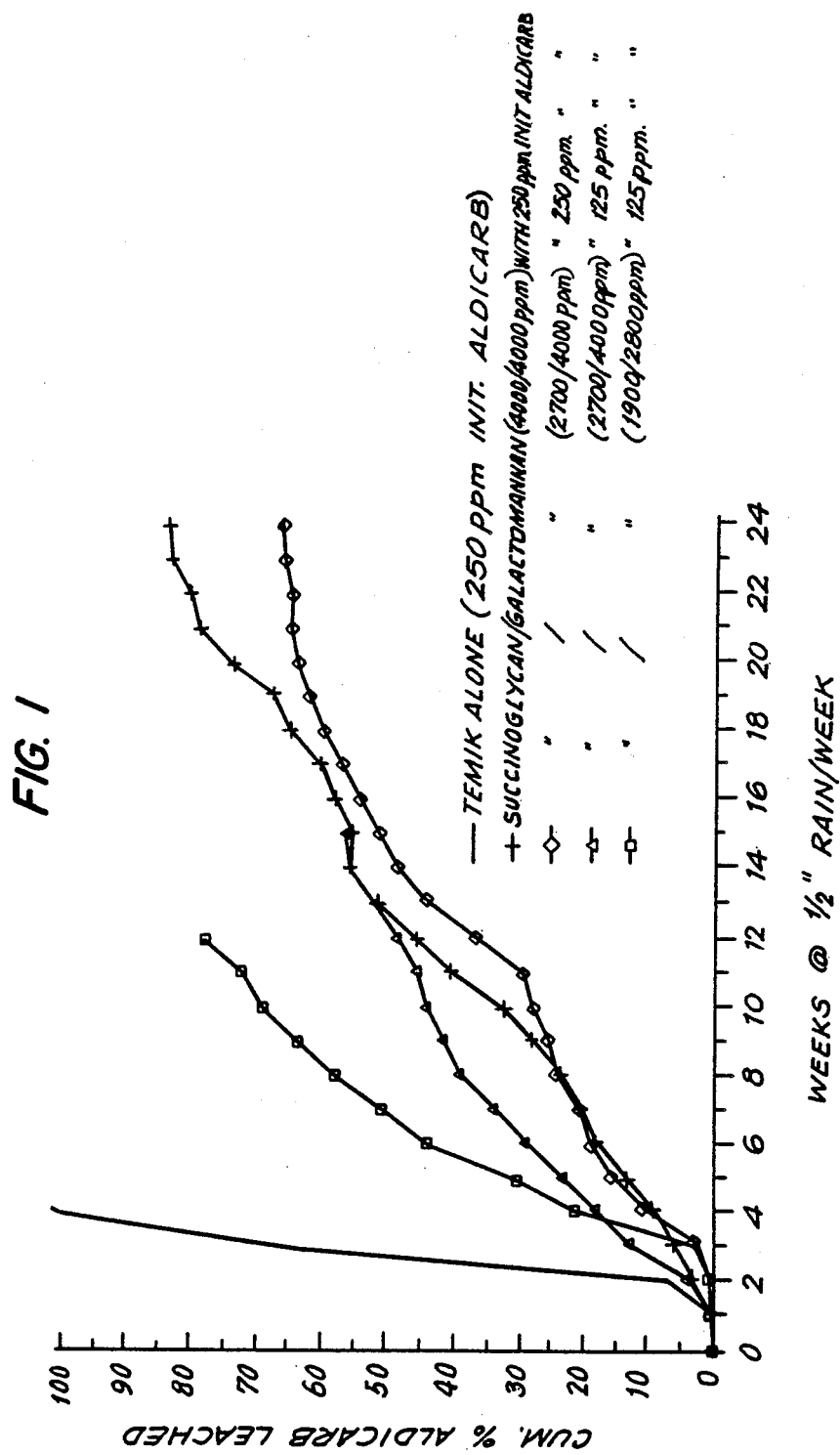

According to one embodiment of the present invention, leaching of agricultural chemicals, and decomposition products thereof, away from the site of application is substantially reduced by administering the agricultural chemicals dispersed in an aqueous gel-forming composition. Thus, due to its controlled release, the agricultural chemical remains available to the roots of the plants for a longer period of time and less is available to contaminate ground water.

In one embodiment, the aqueous gel-forming composition of the present invention is formed by combining an effective amount of a water-soluble polymer with an effective amount of at least one polyvalent metal cation capable of cross-linking the water soluble polymer. The water-soluble polymer is selected from the group consisting of polymers produced by bacteria of the genus Xanthomonas, polymers produced by bacteria of the genera Agrobacterium and Pseudomonas, hydroxyethylcarboxynethylcellulose, carboxymethylcellulose, guar gums, polyacrylamides, and derivatives thereof.

Polymers produced by bacteria of the genus Xanthomonas are commonly referred to as Xanthan gums. The xanthan gum employed in the present invention includes the commercially available form of gum such as FLOCON$^R$ Biopolymer 4800 (Pfizer). Also of interest are the materials described in U.S. Pat. No. 3,717,452 of which columns 2, 3 and 4 are expressly incorporated into the present specification by reference to show a method of preparing the xanthan gum reactant. Xanthan gum is a complex polysaccharide having a molecular weight of over one million, with a cellulose-like backbone composed of repeating β-D-(1-4) glucose units, with acetyl mannose, glucuronic acid, and mannose partially modified with pyruvate ketal groups in side-chains attached β-D-(1-3) to each alternate backbone glucose unit. Xanthan derivatives can also be employed, for example, a xanthan gum which is partially deacetylated and/or partially depyruvated.

Polymers produced by bacteria of the genus Agrobacterium and Pseudomonas correspond to those heteropolysaccharides documented in the prior art as succinoglycan, succinoglucan, succinoglycan-like polymers and succinoglucan-like polymers, all hereinafter referred to as succinoglycans. Succinoglycans are heteropolysaccharides comprised of galactose and 6.0–9.0 moles of glucose for each mole of galactose. These succinoglycans are substituted by acidic functional groups imparting a net negative charge to the heteropolysaccharide. The heteropolysaccharide additionally contains variable proportions of acid residues such as pyruvate, succinate and acetate. These succinoglycans are produced by bacteria of the genera Agrobacterium and Pseudomonas, with preferred succinoglycans being those produced by the species *Agrobacterium radiobacter* and *Agrobacterium tumefaciens*.

Other preferred water soluble polymers include carboxymethylcellulose, hydroxyethylcarboxymethylcellulose, guar gums, polyacrylamides, and derivatives thereof. These polymers are all commercially available and methods for preparing derivatives of these polymers are also well known.

The cross-linking agents employed in the aqueous gel-forming composition of one embodiment of the present invention are preferably polyvalent metal cations. These polyvalent metal cations are selected from metals in Groups III to VIII of the Periodic Table of the Elements. In the present invention, the polyvalent metal cation is selected from the group consisting of aluminum (III), tin (IV), chromium (III), antimony (V), iron (III), titanium (IV) and zirconium (IV).

The metal cations are used in the form of water-soluble compounds yielding polyvalent cations on dissolution. Examples of these compounds include aluminum acetate, aluminum chloride, aluminum citrate, aluminum sulfate, chromium chloride, and other chromium (III) compounds (Volan$^R$, E. I. Dupont de Nemours Co.), ferric chloride, stannic chloride, antimony compounds (SBA-163, Amspec, Gloucester, N.J.), titanium compounds (TYZOR$^R$ AA, E. I. Dupont de Nemours Co.), and zirconium compounds (ZIRTECH$^R$ AA, Zirtech, Inc. Gainesville, Fla.), and zirconium oxychloride (Atomergic Chemetals Corp., Plainview, N.Y.).

Metal compounds which can also be used in the practice of the present invention are water-soluble compounds of polyvalent metals wherein the metal is present in a valence state which is capable of being reduced to a lower polyvalent valence state. Examples of such compounds include ammonium chromate, ammonium dichromate, the alkali metal chromates and the alkali metal dichromates. The above listed metal compounds are encompassed by the term "polyvalent metal cation". Combinations of two or more polyvalent metal cations, i.e., chromium and aluminum, chromium, aluminum and zirconium, can also be used.

The aqueous gel-forming composition of the present invention is formed by combining a suitable polymer selected from the previously described polymers with an effective amount of a polyvalent metal cation capable of cross-linking the chosen polymer. The polymer is generally used in an amount varying from about 0.05 to about 1.0 per cent by weight of the aqueous medium and the polyvalent metal cross-linking agent is generally used in an amount ranging from about 0.003 to about 0.1 per cent by weight of the aqueous medium.

Another preferred aqueous gel-forming composition is formed by combining an aqueous polymerizable silicate with an acid-generating polymerization catalyst. By the term "polymerizable silicate" is meant an aqueous, monomeric form of a silicate salt, such as sodium silicate, commonly called water glass, magnesium silicate, aluminum silicate, etc., all of which are capable of being polymerized.

By the term "acid-generating polymerization catalyst" is meant any organic acid derivative such as amides, esters, sulfonamides, etc., which upon hydrolysis will generate the free acid. One especially preferred acid-generating polymerization catalyst is formamide. Other acid-generating polymerization catalysts include ethyl acetate, glucono delta-lactone, etc. The polymerization reaction proceeds via the generation of the acid upon hydrolysis which then initiates the cross-linking of the monomeric, aqueous, silicates to the polymerized forms.

If desired, additional polymerization catalyst buffering compounds may be incorporated into the polymerizable silicate gel-forming composition. For instance, it has been found that the addition of sodium bicarbonate not only acts as a buffer but also results in the formation of a gel-forming composition into which the agricultural chemical is more evenly dispersed.

In forming the polymerizable silicate/acid generating polymerization catalyst gel-forming composition, the acid generating polymerization catalyst is used in an amount ranging from about 0.3 to about 1.0 percent by weight of the aqueous polymerizable silicate compound.

If the polymerization catalyst buffering agent is added to the aqueous polymerizable silicate/acid generating polymerization catalyst gel forming composition, it is usually added in an amount ranging from about 0.3 to about 1.0 percent, by weight, of the aqueous polymerizable silicate compound.

Another preferred aqueous gel-forming composition is formed by cross-linking polymers produced by bacteria of the genera Agrobacterium and Pseudomonas with a galactomannan. Galactomannans are comprised of linear mannose units with galactopyranose units attached to the linear chain. The ratio of galactose to mannose units varies from 1:3 to 1:6. Preferred galactomannans include guar gum and locust bean gum.

Guar gum is derived from the seed of the guar plant, *Cyanopsis tetragonolobus*. The commercially available gum is substantially pure endosperm from that seed. The pure gum can be used in the process or composition of the present invention; however, derivatives such as oxidized guar gum, carboxyethylated guar gum and hydroxyalkylated guar gums can also be used. The hydroxyalkyl guar gum derivatives include hydroxyethyl and hydroxypropylguar.

Locust bean gum is derived from the seeds of the tree *Ceratonia siliqua*, or the carob tree. The carob, an evergreen that grows to 10 meters, produces pods 10–20 cm long and 2–5 cm wide. Pods are shaken from the trees and are transported to kibbling machines where the pods are broken open and the beans freed. The beans are soaked in water and then milled to remove the shell, release the germ and free the endosperm for later grinding and sifting. The ground endosperm, milled as free of protein as possible, is the commercial gum of industry. Derivatives of locust bean gum such as hydroxyalkyl locust bean gum and phosphated locust bean gums can also be used in the present invention.

In forming the succinoglycan/galactomannan gel-forming composition, the proportion of each ingredient can vary widely. In the case of a succinoglycan/guar gum gel-forming composition, the gel forming compositions can contain from about 5 to about 95 percent by weight of the succinoglycan and from about 5 to about 95 percent by weight of the guar gum. Similar weight ratios can be used if a succinoglycan/locust bean gum gel-forming composition is desired.

Other gel-forming compositions which can be used in the present invention are formed by combining compounds selected from the group consisting of phenol, catechol, resorcinol, hydroquinone, sulfomethylated melamines, and aminomethylated polyacrylamides, with an aldehyde or dialdehyde cross-linking agent of from 1 to 6 carbon atoms.

In forming a phenol, resorcinol, catechol or hydroquinone/aldehyde or dialdehyde gel-forming composition, the procedures described in U.S. Ser. No. 656,801, now U.S. Pat. No. 4,708,974, incorporated herein by reference, are followed. In this application, the gel forming composition is formed by combining the phenolic compound with the aldehyde to yield a gel-forming composition wherein the total concentration of each is from about 0.25 to about 5.0 weight percent. A particularly preferred gel-forming composition is formed by combining resorcinol and formaldehyde at a pH of between 5 and 10 to yield a gel-forming composition wherein the total concentration of the two components is from about 0.25 to about 5.0 weight percent.

Sulfomethylated melamines are formed by reacting a salt of sulfurous acid with melamine and the resultant compound is combined with an aldehyde to yield a gel-forming composition.

Aminoalkylated polyacrylamides are prepared by the Mannich reaction of the appropriate polyacrylamide with formaldehyde and a dialkylamine under basic conditions. These aminoalkylated polyacrylamides are then combined with an aldehyde or dialdehyde to yield a gel-forming composition. An especially preferred gel-forming composition is formed by combining aminomethylpolyacrylamide with glyoxal.

The term "aqueous medium" is used generically in the present specification and in the claims. This term includes fresh water, brines, tap and distilled water and other aqueous media with or without additives which can be gelled in accordance with the invention.

In the process of the present invention, an agricultural chemical is dispersed in the gel-forming composition. The "agricultural chemical" referred to in the present invention is selected from the group consisting of pesticides, herbicides, and fumigants.

The following non-limiting systemic pesticides can be dispersed in the aqueous gels of the present invention. It is to be understood that this listing is not intended to limit the applicability of the present invention. The common or generic name is given first, followed by the chemical name.

aldicarb: 2-methyl-2-(methylthio)propanal 0-[(methylamino)carbonyl]oxime captan: 3a,4,7,7a-tetrahydro-2[trichloromethyl)thio]-1H-isoindole-1,3(2H)-dione carbaryl: 1-naphthyl-N-methylcarbamate carbofuran: 2,3-dihydro-2,2-dimethyl-7-benzofuranyl methylcarbamate as well as other systemic pesticides, including phosphorothioates and phosphorodithioates such as:

demeton: phosphorothioic acid 0,0-diethyl 0-[2-(ethylthio)ethyl]ester diazinon phosphorothioic acid 0,0 diethyl 0-[4-methyl-2-(isopropyl)-6-pyrimidinyl ester dichlorofenthion: phosphorothioic acid 0-2,4-dichlorophenyl 0,0-diethyl ester dimethoate: phosphorodithioic acid 0,0-dimethyl S-[2-methylamino)-2-oxoethyl]ester disulfoton: phosphorodithioic acid 0,0-diethyl S-[2-(ethylthio)ethyl]ester endosulfan: 6,7,8,9,10,10 hexachloro-1,5,5a,6,-9,9a-hexahydro-6,9-methano-2,4,3 benzodioxathiepin-3-oxide fenamiphos: ethyl 3-methyl-4-(methylthio)phenyl (1-methylethyl)phosphoroamidate ferbam: Ferric dimethyldithiocarbamate fonofos: ethylphosphorodithioic acid 0-ethyl S-phenyl ester fenbutatin oxide hexakis (2-methyl-2-phenylpropyl)distannoxane metalaxyl: N-(2,6-dimethylphenyl)-N-(methoxyacetyl)alanine methyl ester oxamyl methyl N',N'-dimethyl-N-[(methylcarbamoyl)oxy]-1-thiooxamimidate oxydemeton-methyl: S-[2-(ethylthio-ethyl 0,0-dimethyl phosphorothioate phorate: phosphorodithioic acid 0,0-diethyl S-[(ethylthio)methyl]ester terbufos phosphorodithioic acid S-[[(1,1-dimethylethyl)thio]methyl]0,0 diethyl ester thiabendazole: 2-(4-thiazolyl)-1H-benzimidazole thionazin: phosphorothioic acid 0,0-diethyl-0-pyrazinyl ester Fumigants which can be used in the present invention include N-methyldithiocarbamate, chloropicrin, dazomet, aluminum phosphide and methyl isothiocyanate. Since fumigants are noted for rapid decomposition and volatilization, the process of the present invention is also useful for preventing the rapid release of decomposition products of the fumigants into the surrounding atmosphere.

The following is a non-limiting listing of herbicides which can be used in the present invention. The common name is given first, followed by the chemical name.

alachlor: 2-chloro-2',6'-diethyl-N-(methoxymethyl)acetanilide atrazine: 6-chloro-N-ethyl-N-(1-methylethyl)-1,3,5-triazine-2,4-diamine dinoseb: 3-methyl-2-butenoic acid 2-(1-methylpropyl)4,6-dinitrophenyl ester metribuzin: 4-amino-6-(1,1-dimethylethyl)-3-methylthio)-1,2,4-triazin-5(4H)-one simazine: 6-chloro-N,N'-diethyl-1,3,5-triazine-2,4-diamine.

The agricultural chemical can be incorporated into the aqueous gel-forming composition using a variety of methods. One method is to combine the polymer or compound, cross-linking agent and aqueous medium so as to start the gelation process, and then apply the aqueous gel-forming composition to the soil surrounding the seedlings. The agricultural chemical is then dispersed in the aqueous gel-forming composition. A preferred method is to disperse the agricultural chemical into the gel-forming composition and apply the agricultural chemical/gel-forming composition to the soil.

The present invention is also directed to novel compositions of the agricultural chemical dispersed in the gel-forming composition. The gel-forming composition is formed by combining the previously described polymers or compounds with the previously described polyvalent metal cross-linking agents, galactomannan or other cross-linking agent or polymerization catalyst and then dispersing the agricultural chemical in the gel-forming composition. It has also been found that more uniform dispersion of the agricultural chemical can be accomplished by combining the polymer, aqueous medium and agricultural chemical to form a dispersed solution and then adding the polyvalent metal, galactomannan or other cross-linking agent or polymerization catalyst to start the gelation process. In the composition of the present invention, the agricultural chemical is present in an amount ranging from about 0.002 to about 0.1 percent by weight and the gel forming composition is present in an amount ranging from about 0.05 to about 1.0 percent, by weight, of the composition.

In the case of an aqueous gel-forming composition formed by combining a xanthan with a galactomannan, it has surprisingly been found that application of an agricultural chemical dispersed in this gel forming composition into the soil surrounding the plants surprisingly results in decreased leaching away from the site of application and controlled release.

As an agricultural chemical composition, the gel-forming composition compositions of the present invention can be applied to the soil at a rate of 1 to 100 pounds per acre.

Having described the invention in general terms, reference is now made to specific examples thereof.

EXAMPLE 1

Gel-forming compositions were prepared using the following polymers and polyvalent metal cross-linking agents.

|  | ppm |  |
|---|---|---|
| carboxymethylcellulose | (a) 6000 | (b) 3000 |
| aluminum (III) | (a) 150-250 | (b) 114-190 |
| Xanthan | (a) 4000 | (b) 3000 |
| aluminum (III) | (a) 137-229 | (b) 107-177 |
| succinoglycan | (a) 3000 |  |
| aluminum (III) | (a) 107-177 |  |

EXAMPLE 2

Each of the gel-forming compositions prepared in Example 1 were admixed with Aldicarb (TEMIK$^R$ Union Carbide). The TEMIK$^R$ 15-G (15% aldicarb) granules were predispersed in the polymer solution (polymer & aqueous medium) prior to adding the aluminum (III) cross-linking agent. The aldicarb/gel plugs were emplaced at a depth of 12 to 24 inches in seedling pots. The mixtures were covered with soil and orange seedlings were planted. The experimental protocol is summarized in Table 1.

TABLE I

Citrus Seedling Trial
Seedling variety: Carizzo citrange orange

| Seedlings Sample No. | Gel Sample | Gel Concentration PPM | Temik[a] mg/sample |
|---|---|---|---|
| 1, 2, 3 | CMC[c]/Al(III)[b] | 6000 | 115.0 |
| 4, 5, 6 | CMC/Al(III) | 6000 | 57.0 |
| 7, 8, 9 | none | 0 | 115.0 |
| 10, 11, 12 | none | 0 | 57.0 |
| 13, 14, 15 | CMC/Al(III) | 6000 | 115.0 |
| 16, 17, 18 | CMC/Al(III) | 6000 | 115.0 |
| 19, 20, 21 | CMC/Al(III) | 6000 | 115.0 |
| 22, 23, 24 | CMC/Al(III) | 6000 | 115.0 |
| 25, 26, 27 | CMC/Al(III) | 3000 | 115.0 |
| 28, 29, 30 | Xanthan/Al(III) | 3000 | 115.0 |
| 31, 32, 33 | Xanthan/Al(III) | 4000 | 115.0 |
| 34, 35, 36 | succinoglycan/Al(III) | 3000 | 115.0 |

[a] 115 mg = 17,250 μg active aldicarb in 35 in$^3$ gel volume, corresponding to 30 ppm
[b] as aluminum dibasic acetate (Niaproof, Niacet Corporation, Niagara Falls, N.Y.)
[c] sodium carboxymethylcellulose (Hercules 7-H, Wilmington, DE)
*No toxic moieties detected; detection limit is 1.2-34 micrograms TTR The seedling boxes were watered initially with 400 cc of water within 2 to 3 hours after planting. Afterwards, the plants were watered with 100 cc of water per week. Leachate assays from each seedling box were performed using EPA method 531 (High Performance Liquid Chromatography). Total Leachate Volumes (TLV) were recorded and the following additional calculations were performed.

ppm total toxic residue (TTR) = ppm aldicarb (AS) + ppm aldicarb sulfoxide (ASX) + ppm aldicarb sulfone (ASN)    (a)

μg TTR found = ppm TTR × ml TLV    (b)

Percent Original Temik Lost to Leachate = 100 × cumulative g TTR/17250 or /8625 (high or low Temik doses)    (c)

The results after six months are presented in Tables II–III.

TABLE II

ORANGE SEEDLINGS TEMIK LEACHATE ASSAY RESULTS
Total Toxic Residue (Aldicarb + Sulfoxide + Sulfone)
in Collected Leachate - Average of 3 Boxes

| Set/Month Conditions | Micrograms Each Month/Cumulative | | | | | | |
|---|---|---|---|---|---|---|---|
|  | 1 | 2 | 3 | 4 | 5 | 6 |  |
| 1–3 | 183 | 832 | 1060 | 1090 | 647 | 407 | Hi Temik, hi |
|  | 183 | 1015 | 2075 | 3165 | 3812 | 4219 | CMC gel |
| 4–6 | 96 | 141 | 161 | 466 | 290 | 195 | Lo Temik, hi |
|  | 96 | 237 | 398 | 864 | 1154 | 1349 | CMC gel |
| 7–9 | 6090 | 3810 | 1020 | 531 | 380 | 588 | Hi Temik, no gel |
|  | 6090 | 9900 | 10920 | 11451 | 11831 | 12419 |  |

TABLE II-continued

ORANGE SEEDLINGS TEMIK LEACHATE ASSAY RESULTS
Total Toxic Residue (Aldicarb + Sulfoxide + Sulfone)
in Collected Leachate - Average of 3 Boxes

| Set/Month Conditions | Micrograms Each Month/Cumulative | | | | | | |
|---|---|---|---|---|---|---|---|
| | 1 | 2 | 3 | 4 | 5 | 6 | |
| 10–12 | 680 | 1040 | 774 | 582 | 280 | 425 | Lo Temik, no gel |
| | 680 | 1720 | 2494 | 3076 | 3356 | 3781 | |
| 13–15 | * | * | * | * | * | * | No Temik, hi CMC gel |
| 22–24 | 132 | 1150 | 1210 | 949 | 810 | 380 | Hi Temik, hi CMC gel |
| | 132 | 1282 | 2492 | 3441 | 4251 | 4631 | (same as 1–3) |
| 25–27 | 1930 | 1360 | 1070 | 287 | 243 | 190 | Hi Temik, lo cmc gel |
| | 1930 | 3290 | 4360 | 4647 | 4890 | 5080 | |
| 28–30 | 1550 | 818 | 947 | 265 | 281 | 418 | Hi Temik, lo xanthan gel |
| | 1550 | 2368 | 3315 | 3580 | 3861 | 4279 | |
| 31–33 | 1180 | 2010 | 1270 | 420 | 252 | 538 | Hi Temik, hi xanthan gel |
| | 1180 | 3190 | 4460 | 4880 | 5132 | 5670 | |
| 34–36 | 939 | 2380 | 1550 | 663 | 440 | 729 | Hi Temik, succinoglycan gel |
| | 939 | 3319 | 4869 | 5532 | 5972 | 6701 | |

*No toxic moities detected; detection limit is 1.2-34 micrograms TTR

\*No toxic moieties detected; detection limit is 1.2-34 micrograms TTR

TABLE III

ORANGE SEEDLING TEMIK/GEL LEACHATE STUDY
PERCENT OF ORIGINAL TEMIK
LOST TO LEACHATE AFTER

| Month | 1 | 2 | 3 | 4 | 5 | 6 |
|---|---|---|---|---|---|---|
| High Temik/Gel | 0.9 | 6.7 | 13 | 19 | 23 | 26 |
| High Temik/No Gel | 35 | 57 | 63 | 66 | 69 | 72 |
| % Reduction by Gel | 97 | 88 | 79 | 71 | 66 | 64 |
| Low Temik/Gel | 1.1 | 2.8 | 4.4 | 10 | 14 | 16 |
| Low Temik/No Gel | 7.1 | 20 | 29 | 36 | 40 | 45 |
| % Reduction by Gel | 84 | 86 | 84 | 72 | 66 | 65 |

EXAMPLE 3

Gel plugs (50 cc conical frustums) containing Temik$^R$ 15G were prepared by direct blending of xanthan (2700–4000 ppm), and a galactomannan (guar or locust bean gum; 2800–4000 ppm) with Temik 15G granules (250 ppm aldicarb). The gel plugs were placed in 2" diameter sand columns. Each column was watered at a constant drip rate of 1.3 cc/min. (to simulate ½" rain/week) for 25 minutes, followed by 4 hours (minimum) drainage. Eluent (leachate) was analyzed for active aldicarb. The controls, Temik 15G alone (250 ppm aldicarb) and non-gelled guar (8000 ppm) containing Temik, were similarly emplaced in sand (same volume and location as gel plugs) and exposed to the same watering treatment and leachate analyses. The results (FIG. 2) show high concentrations (8000 ppm) of non-gelled guar could significantly delay aldicarb release into soil leachate but a substantial burst of aldicarb would still be released into the soil after seven or eight weeks under lab simulated soil and rainfall conditions (e.g. Florida citrus groves). By contrast, the gelled xanthan/galactomannan plugs released the aldicarb into the soil at desirable, relatively constant low levels over a much longer period, thereby greatly reducing the potential for aldicarb groundwater contamination.

EXAMPLE 4

Gel plugs (50 cc conical frustums) containing Temik$^R$ 15G were prepared by direct blending of succinoglycan (1900–4000 ppm), and a galactomannan (guar; 2800–4000 ppm) with Temik 15G granules (250 ppm aldicarb). The gel plugs were placed in a 2" diameter ×12" long glass permeameter tube and surrounded by washed sea sand. Each column was watered at a constant drip rate of 1.3 cc/min. (to simulate ½" rain/week) for 25 minutes, followed by 4 hours (minimum) drainage. Eluant (leachate) was analyzed for active aldicarb. The controls, Temik 15G alone (250 ppm aldicarb) and non-gelled guar (8000 ppm) containing Temik, were similarly emplaced in sand (same volume and location as gel plugs) and exposed to the same watering treatment and leachate analyses. The results (FIG. 3) show high concentrations (8000 ppm) of non-gelled guar could significantly delay aldicarb release into soil leachate but a substantial burst of aldicarb would still be released into the soil after seven or eight weeks under lab simulated soil and rainfall conditions (e.g. Florida citrus groves). By contrast, the gelled succinoglycan/galactomannan plugs released the aldicarb into the soil at desirable, relatively constant low levels over a much longer period, thereby greatly reducing the potential for aldicarb groundwater contamination.

EXAMPLE 5

A composition for controlling the release of agricultural fumigants (CRC) was prepared as follows. Measured amounts of a diluted fumigant (I) (the concentrate, 33% N-methyldithiocarbamate, is marketed as "Soil-Prep" by Wilbur-Ellis Co., Fresno, Calif.) and a pregelant agent (II) were introduced in a beaker. Component I consisted of 50% Soil-Prep and 50% distilled water. Component II was prepared as follows. Weighed amounts of three components: sodium bicarbonate (IIA), formamide (IIB) and water glass (IIC) (30% aqueous silicate solution) were combined in the following order and amounts:

| | Percentages by wt. |
|---|---|
| 1 Water, distilled | 60.1 |
| 2 IIA | 1.8 |
| 3 IIB | 1.0 |
| 4 IIC | 37.1 |

Component IIA was completely dissolved in water and the prescribed amount of IIB was added. This aqueous mixture was then added to component IIC and vigorously mixed. Component I was then added to mixture II in the ratio of 0.133 (ml/g) and vigorously stirred for 15 to 30 seconds.

The efficacy of the CRC as a release profile modifying agent was evaluated as follows. An aliquot of CRC was injected 3 to 5 inches below the soil surface of several test chambers loaded with 150 g of a sandy-loam soil. Dosages were set equivalent to 25 gallons of Soil-Prep per solid acre. A different chamber was opened to the atmosphere for a predetermined length of time (e.g. 0, 24, 30, 48 hours). After the prescribed length of time had elapsed, chambers were closed and 100 ul headspace gas samples were assayed hourly via gas chromatography until methyl isothiocyanate (MIT) concentrations had equilibrated. The results obtained are shown in the graph below (FIG. 4). The efficacy of straight fumigant (time when equilibrium headspace MIT concentration > 150 ppm) was extended approximately three-fold when CRC gelant agent was used.

EXAMPLE 6

Example 5 was repeated in preparing a CRC agent having the composition:

|   | Percentages by wt. |
|---|---|
| 1 Water, distilled | 60.4 |
| 2 IIA | 3.0 |
| 3 IIB | 6.6 |
| 4 IIC | 30.0 |

Figure 6:
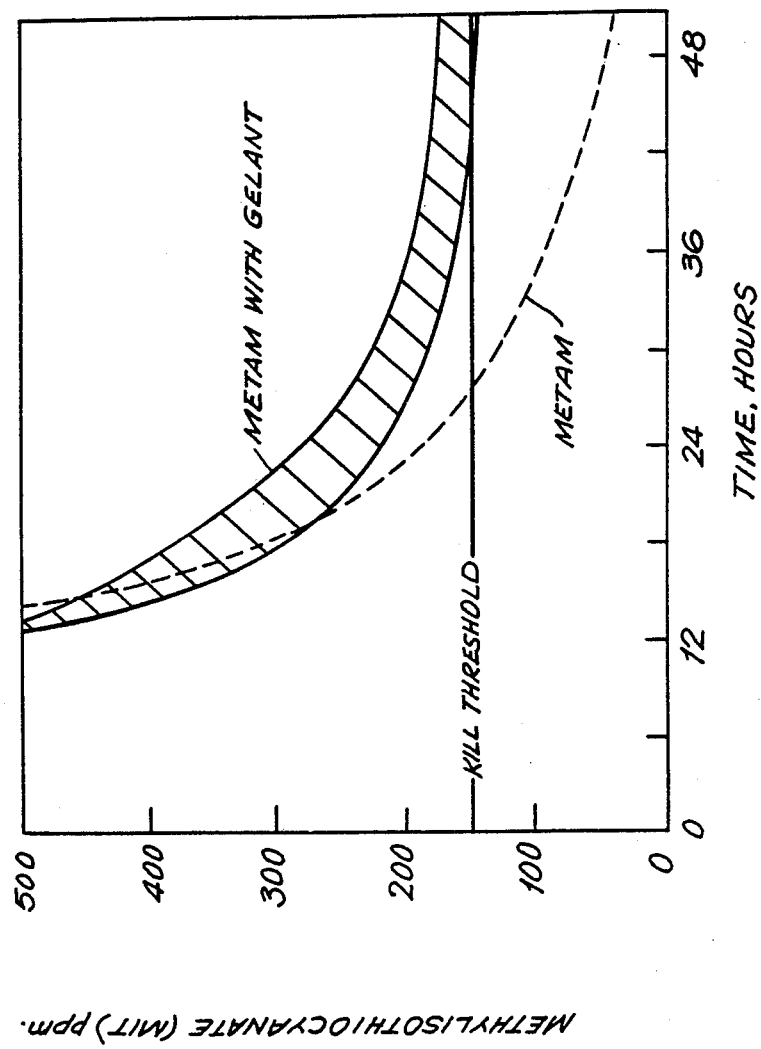
FIG. 6 is a graphical representation of methylisothiocyanate (MIT) release with and without the N-methyldithiocarbamate precursor being incorporated into a gel-forming composition of the present invention.

The results obtained are shown in the graph below (FIG. 6).

Extended fumigant efficacy and reduced fumigant residual lag times (no greater than 144 hours) were obtained.

EXAMPLES 7-11

Additional examples were prepared with the CRC agent having the compositions shown in the table below.

| Example | I gal/acre* | IIC (%) | IIB (%) | IIA (%) | II/II (ml/g) | Kill Time (hour) |
|---|---|---|---|---|---|---|
| 7 | 50 | 37 | 6.7 | 1.5 | 0.067 | 48 |
| 8 | 50 | 38 | 4.2 | 1.5 | 0.067 | 40 |
| 9 | 50 | 37 | 2.0 | 1.7 | 0.093 | 44 |
| 10 | 50 | 37 | 1.0 | 1.8 | 0.107 | 46 |
| 11 | 50 | 37 | 2.0 | 1.7 | 0.130 | 48 |
| 5 | 50 | 37 | 1.0 | 1.8 | 0.133 | 48 |
| 5 | 50 | 0 | 0.0 | 0.0 | — | 17 |
| 5 | 100** | 0 | 0.0 | 0.0 | — | 27 |

*Solid acre.
**Typical application level.

We claim:

1. A process for the controlled release and substantial reduction of leaching from the site of application of agricultural chemical selected from the group consisting of pesticides, herbicides and fumigants, and decomposition products thereof, comprising administering said chemical dispersed in an aqueous gel-forming composition formed by combining an aqueous, polymerizable silicate with an acid generating polymerization catalyst.

2. A process according to claim 1 wherein said aqueous polymerizable silicate is sodium silicate.

3. A process according to claim 2 wherein said acid generating polymerization catalyst is formamide.

4. A process according to claim 1 wherein said agricultural chemical is an organic pesticide.

5. A process according to claim 4 wherein said organic pesticide is 2-methyl-2-(methylthio) propanal 0-[(methylamino)-carbonyl]oxime.

6. A process according to claim 1 wherein said agricultural chemical is a fumigant.

7. A process according to claim 1 wherein said agricultural chemical is an herbicide.

8. A process according to claim 1 further comprising the addition of a polymerization catalyst buffering compound.

9. A process according to claim 8 wherein said polymerization catalyst buffering compound is sodium bicarbonate.

10. A process according to claim 8 wherein said agricultural chemical is an organic pesticide.

11. A process according to claim 10 wherein said organic pesticide is 2-methyl-2(methylthio)propanol O-[(methylamino)-carbonyl]oxime.

12. A process according to claim 8 wherein said agricultural chemical is a fumigant.

13. A process according to claim 8 wherein said agricultural chemical is an herbicide.

14. A composition for the control of insects, nematodes, undesired vegetation, and fumigation of soil, said composition exhibiting controlled release and substantially reduced leaching of the insecticidally, nematicidally, or herbicidally, active agent from the site of application, said composition comprising an effective amount of an insecticidally, herbicidally, nematicidally active agent dispersed in a gel-forming composition, said gel-forming composition formed by combining an aqueous polymerizable silicate with an acid generating polymerization catalyst.

15. A composition according to claim 14 wherein said aqueous, polymerizable silicate is aqueous sodium silicate.

16. A composition according to claim 14 wherein said acid-generating polymerization catalyst is formamide.

17. A composition according to claim 14 wherein said insecticidally active agent is an organic pesticide.

18. A composition according to claim 17 wherein said organic pesticide is 2-methyl-2-(methylthio) propanol O-[(methylamino)-carbonyl]oxime.

19. A composition according to claim 14 further comprising the addition of a polymerization catalyst buffering agent.

20. A composition according to claim 19 wherein said polymerization catalyst buffering agent is sodium bicarbonate.

21. A composition according to claim 19 wherein said insecticidally active agent is an organic pesticide.

22. A composition according to claim 21 wherein said organic pesticide is 2-methyl-2-(methylthio)propanol O-[(methylamino)-carbonyl]oxime.

* * * * *